(12) United States Patent
Moussa (10) Patent No.: US 11,426,406 B2
(45) Date of Patent: Aug. 30, 2022

(54) COMPOSITIONS AND METHODS FOR TREATING LYSOSOMAL STORAGE DISORDERS

(71) Applicant: GEORGETOWN UNIVERSITY, Washington, DC (US)

(72) Inventor: Charbel Moussa, Germantown, MD (US)

(73) Assignee: GEORGETOWN UNIVERSITY, Washington, DC (US)

( * ) Notice: Subject to any disclaimer, the term of this patent is extended or adjusted under 35 U.S.C. 154(b) by 0 days.

(21) Appl. No.: 16/484,780

(22) PCT Filed: Feb. 9, 2018

(86) PCT No.: PCT/US2018/017606
§ 371 (c)(1),
(2) Date: Aug. 8, 2019

(87) PCT Pub. No.: WO2018/148533
PCT Pub. Date: Aug. 16, 2018

(65) Prior Publication Data
US 2020/0000804 A1    Jan. 2, 2020

Related U.S. Application Data

(60) Provisional application No. 62/456,821, filed on Feb. 9, 2017.

(51) Int. Cl.
*A61K 31/506* (2006.01)
*A61K 31/496* (2006.01)
*A61K 31/5377* (2006.01)
*A61K 45/06* (2006.01)

(52) U.S. Cl.
CPC .......... *A61K 31/506* (2013.01); *A61K 31/496* (2013.01); *A61K 31/5377* (2013.01); *A61K 45/06* (2013.01)

(58) Field of Classification Search
CPC ............................ A61K 31/506; A61K 31/496
See application file for complete search history.

(56) References Cited

U.S. PATENT DOCUMENTS

| | | |
|---|---|---|
| 6,002,008 A | 12/1999 | Wissner et al. |
| 7,105,530 B2 | 9/2006 | Boloor et al. |
| 7,169,791 B2 | 1/2007 | Breitenstein et al. |
| 7,687,512 B2 | 3/2010 | Bilbe |
| 2012/0190642 A1 | 7/2012 | Grynkewicz et al. |

(Continued)

FOREIGN PATENT DOCUMENTS

| | | |
|---|---|---|
| WO | 2016014542 A1 | 1/2016 |
| WO | 2016014551 A1 | 1/2016 |

OTHER PUBLICATIONS

Kothiwale et al, Drug Discovery Today (2015), vol. 20(2), pp. 255-261 (Year: 2015).*

(Continued)

*Primary Examiner* — Craig D Ricci
*Assistant Examiner* — Janet L Coppins
(74) *Attorney, Agent, or Firm* — Kilpatrick Townsend & Stockton LLP (57) ABSTRACT

Provided herein are methods of treating a lysosomal storage disorder (LSD) in a subject and methods of promoting lysosomal clearance in one or more cells of a subject.

7 Claims, 6 Drawing Sheets

(56) References Cited

U.S. PATENT DOCUMENTS

| | | | |
|---|---|---|---|
| 2013/0072482 A1 | 3/2013 | Yang et al. | |
| 2014/0038920 A1* | 2/2014 | Ballabio | A61K 31/437 514/80 |
| 2014/0135296 A1 | 5/2014 | Deretic et al. | |
| 2016/0051629 A1 | 2/2016 | Futerman et al. | |
| 2017/0029413 A1 | 2/2017 | Holladay et al. | |

OTHER PUBLICATIONS

Beck, Hum Genet (2007), vol. 12, pp. 1-22. (Year: 2007).*
Weisberg et al, Cancer Cell (2005), vol. 7, pp. 129-141. (Year: 2005).*
Alvarez et al, The Faseb Journal (2008), vol. 22, pp. 3617-3627. (Year: 2008).*
International Application No. PCT/US2018/017606, "International Preliminary Report on Patentability", dated Aug. 22, 2019, 7 pages.
Bhaumik et al., "A mouse model for mucopolysaccharidosis type III A (Sanfilippo syndrome)", Glycobiology vol. 9, 1999, pp. 1389-1396.
Bhattacharyya et al., "A novel missense mutation in lysosomal sulfamidase is the basis of MPS III A in a spontaneous mouse mutant", Glycobiology, vol. 11, Issue 1, Jan. 1, 2001, pp. 99-103.
Al-Naamani et al., "Imatinib as rescue therapy in a patient with pulmonary hypertension associated with Gaucher disease", Chest. Sep. 2014;146(3), pp. e81-e83.
Alvarez, "Imatinib therapy blocks cerebellar apoptosis and improves neurological symptoms in a mouse model of Niemann-Pick type C disease", FASEB J., Oct. 2008, pp. 3617-3627.
Kan et al., "Behavioral deficits and cholinergic pathway abnormalities in male Sanfilippo B mice", Behavioural Brain Research, vol. 312, 2016, pp. 265-271.
Malinowska et al., "Genistein reduces lysosomal storage in peripheral tissues of mucopolysaccharide IIIB mice", Mol Genet Metab. Nov. 2009, vol. 98, Issue 3, pp. 235-242.
Lonskaya et al., "Nilotinib and bosutinib modulate pre-plaque alterations of blood immune markers and neuro-inflammation in Alzheimer's disease models", Neuroscience Jul. 30, 2015, 304, pp. 316-327.
International Application No. PCT/US2018/017606, "International Search Report and Written Opinion", dated Apr. 19, 2018, 9 pages.

* cited by examiner

COMPOSITIONS AND METHODS FOR TREATING LYSOSOMAL STORAGE DISORDERS

This application claims priority to U.S. Provisional Application No. 62/456,821, filed Feb. 9, 2017, which is hereby incorporated in its entirety by this reference.

BACKGROUND

Lysosomal storage disorders represent some of the most devastating of genetic diseases, and the need to develop therapies for these disorders remains largely unmet. Many of these diseases cause damage to the central nervous system (CNS), but the mechanisms underlying such damage are largely unknown. Although the incidence of lysosomal storage disorders is rare (less than about 1:100,000 individuals is affected). Lysosomal storage disorders affect mostly children who often die at a young age, many within a few months or years of birth. Many other children die following years of suffering from various symptoms of their particular lysosomal storage disorder. Therefore, there is a need for compositions and methods to treat lysosomal storage disorders.

SUMMARY

Provided herein are methods of treating a lysosomal storage disorder (LSD) in a subject. The methods comprise administering to the subject having an LSD an effective amount of a tyrosine kinase inhibitor, wherein the tyrosine kinase inhibitor is not Gleevec. Also provided are methods of promoting lysosomal clearance in one or more cells of a subject. The methods comprise administering to the subject an effective amount of a tyrosine kinase inhibitor, wherein the subject has a disorder associated with decreased lysosomal clearance, and wherein the tyrosine kinase inhibitor is not Gleevec.

DETAILED DESCRIPTION

Provided herein are methods of treating a LSD in a subject comprising administering to the subject having an LSD an effective amount of a tyrosine kinase inhibitor, wherein the tyrosine kinase inhibitor is not Gleevec. LSDs are inherited metabolic disorders that result from defects in lysosomal function. In the majority of cases, LSDs are caused by a deficiency of specific enzymes responsible for degradation of lipids and glycoproteins present in lysosomes. In some cases, defective non-enzymatic lysosomal proteins or non-lysosomal proteins involved in lysosomal biogenesis cause LSDs. The progressive lysosomal accumulation of undegraded metabolites results in generalized cell and tissue dysfunction, and, therefore, multi-systemic pathology. LSDs that can be treated using any of the methods provided herein include, but are not limited to, Mucopolysaccharidosis Type I (for example, Hurler syndrome, Hurler-Scheie syndrome and Scheie syndrome), Mucopolysaccharidosis Type I (for example, Hunter syndrome), Mucopolysaccharidosis Type III (for example, Sanfillipo syndrome A, Sanfillipo syndrome B, Sanfillipo syndrome C and Sanfillipo syndrome D), Mucopolysaccharidosis Type IV (for example, Morquio syndrome A and Morquio syndrome B), Mucopolysaccharidosis Type VI (for example, Maroteaux-Lamy syndrome), Mucopolysaccharidosis Type VII (for example, Sly syndrome), Mucopolysaccharidosis Type IX (for example, Natowicz syndrome), Pseudo-Hurler polydystrophy, Tay-Sachs, Gaucher disease, Niemann-Pick disease, Fucosidosis, Galactosialidosis, Globoid-cell leukodystrophy, $G_{M1}$ Gangliosidosis, $G_{M2}$ Gangliosidosis, α-Mannosidosis, Metachromatic leukodystrophy and Pompe disease. The LSDs provided herein are examples of diseases or disorders associated with decreased lysosomal clearance.

The tyrosine kinase inhibitors that can be used in any of the methods described herein include, but are not limited to, tyrosine kinase inhibitors that inhibit one or more receptor tyrosine kinases selected from the group consisting of Abl, PDGFRα, PDGFRβ, DDR 1, DDR2, cKIT, arginase II, Src, Fyn, VEGFR and Zac. In some examples, the tyrosine kinase inhibitor selectively inhibits Abl, PDGFRα, PDGFRβ, DDR 1, DDR2, arginase II, Src, Fyn or VEGR or Zac.

In another example, a class of tyrosine kinase inhibitors for use in the methods described herein is represented by Formula I:

and pharmaceutically acceptable salts and prodrugs thereof.

In Formula I, $R^1$, $R^2$, $R^3$, $R^4$, and $R^5$ are each independently selected from the group consisting of hydrogen, halogen, hydroxyl, cyano, trifluoromethyl, alkoxyl, aryloxyl, substituted or unsubstituted sulfonyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalky .

Also in Formula I, $L^1$ is —$NR^6$— or —$NR^6$—C(O)—, wherein $R^6$ is selected from hydrogen, substituted or unsubstituted alkyl, and substituted or unsubstituted aryl. Optionally, $L^1$ is —NH— or —NH—C(O)—.

Also in Formula I, $L^2$ is absent, substituted or unsubstituted alkoxy, —$R^6$—, or —$NR^6$—C(O)—, wherein $R^6$ is selected from hydrogen, substituted or unsubstituted alkyl, and substituted or unsubstituted aryl. Optionally, $L^2$ is —$OCH_2$—, —$OCH_2$—, —$OCH2CH_2$—, $OCH_2CH_2CH_2$—, —NH—, or —$NCR_3$—.

Additionally in Formula I, X is substituted or unsubstituted aryl or substituted or unsubstituted heteroaryl.

Also in Formula I, Y is substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl.

Examples of Formula I include the following compounds:

Compound 1

(Bosutinib)

Compound 2

(Nilotinib)

Compound 3

(Pazopanib)

Compound 4

(LCB 03-0110)

As used herein, the terms alkyl, alkenyl, and alkynyl include straight- and branched-chain monovalent substituents. Examples include methyl, ethyl, isobutyl, 3-butynyl, and the like. Ranges of these groups useful with the compounds and methods described herein include $C_1$-$C_{20}$ alkyl, $C_2$-$C_{20}$ alkenyl, and $C_2$-$C_{20}$ alkynyl. Additional ranges of these groups useful with the compounds and methods described herein include $C_1$-$C_{12}$ alkyl, $C_2$-$C_{12}$ alkenyl, $C_2$-$C_{12}$ alkynyl, $C_1$-$C_6$ alkyl, $C_2$-$C_6$ alkenyl, $C_2$-$C_6$ alkynyl, $C_1$-$C_4$ alkyl, $C_2$-$C_4$ alkenyl, and $C_2$-$C_4$ alkynyl.

Heteroalkyl, heteroalkenyl, and heteroalkynyl are defined similarly as alkyl, alkenyl, and alkynyl, but can contain O, S, or N heteroatoms or combinations thereof within the backbone. Ranges of these groups useful with the compounds and methods described herein include $C_1$-$C_{20}$ heteroalkyl, $C_2$-$C_{20}$ heteroalkenyl, and $C_2$-$C_{20}$ heteroalkynyl. Additional ranges of these groups useful with the compounds and methods described herein include $C_1$-$C_{12}$ heteroalkyl, $C_2$-$C_{12}$ heteroalkenyl, $C_2$-$C_{12}$ heteroalkynyl, $C_1$-$C_6$ heteroalkyl, $C_2$-$C_6$ heteroalkenyl, $C_2$-$C_6$ heteroalkynyl, $C_1$-$C_4$ heteroalkyl, $C_2$-$C_4$ heteroalkenyl, and $C_2$-$C_4$ heteroalkynyl.

The terms cycloalkyl, cycloalkenyl, and cycloalkynyl include cyclic alkyl groups having a single cyclic ring or multiple condensed rings. Examples include cyclohexyl, cyclopentylethyl, and adamantanyl. Ranges of these groups useful with the compounds and methods described herein include $C_3$-$C_{20}$ cycloalkyl, $C_3$-$C_{20}$ cycloalkenyl, and $C_3$-$C_{20}$ cycloalkynyl. Additional ranges of these groups useful with the compounds and methods described herein include $C_5$-$C_{12}$ cycloalkenyl, $C_5$-$C_{12}$ cycloalkynyl, $C_5$-$C_6$ cycloalkyl, $C_5$-$C_6$ cycloalkenyl, and $C_5$-$C_6$ cycloalkynyl.

The terms heterocycloalkyl, heterocycloalkenyl, and heterocycloalkynyl are defined similarly as cycloalkyl, cycloalkenyl, and cycloalkynyl, but can contain O, S, or N heteroatoms or combinations thereof within the cyclic backbone. Ranges of these groups useful with the compounds and methods described herein include $C_3$-$C_{20}$ heterocycloalkyl, $C_3$-$C_{20}$ heterocycloalkenyl, and $C_3$-$C_{20}$ heterocycloalkynyl. Additional ranges of these groups useful with the compounds and methods described herein include $C_5$-$C_{12}$ heterocycloalkyl, $C_5$-$C_{12}$ heterocycloalkenyl, $C_5$-$C_{12}$ heterocycloalkynyl, $C_5$-$C_6$ heterocycloalkyl, $C_5$-$C_6$ heterocycloalkenyl, and $C_5$-$C_6$ heterocycloalkynyl.

Aryl molecules include, for example, cyclic hydrocarbons that incorporate one or more planar sets of, typically, six carbon atoms that are connected by delocalized electrons numbering the same as if they consisted of alternating single and double covalent bonds. An example of an aryl molecule is benzene. Heteroaryl molecules include substitutions along their main cyclic chain of atoms such as O, N, or S. When heteroatoms are introduced, a set of five atoms, e.g., four carbon and a heteroatom, can create an aromatic system. Examples of heteroaryl molecules include furan, pyrrole, thiophene, imadazole, oxazole, pyridine, and pyrazine. Aryl and heteroaryl molecules can also include additional fused rings, for example, benzofuran, indole, benzothiophene, naphthalene, anthracene, and quinoline. The aryl and heteroaryl molecules can be attached at any position on the ring, unless otherwise noted.

The term alkoxy as used herein is an alkyl group bound through a single, terminal ether linkage. The term aryloxy as used herein is an aryl group bound through a single, terminal ether linkage. Likewise, the terms alkenyloxy, alkynyloxy, heteroalkyloxy, heteroalkenyloxy, heteroalkynyloxy, heteroaryloxy, cycloalkyloxy, and heterocycloalkyloxy as used herein are an alkenyloxy, alkynyloxy, heteroalkyloxy, heteroalkenyloxy, heteroalkynyloxy, heteroaryloxy, cycloalkyloxy, and heterocycloalkyloxy group, respectively, bound through a single, terminal ether linkage.

The term hydroxy as used herein is represented by the formula —OH.

The terms amine or amino as used herein are represented by the formula —$NZ^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above.

The alkoxy, aryloxy, amino, alkyl, alkenyl, alkynyl, aryl, heteroalkyl, heteroalkenyl, heteroalkynyl, heteroaryl, cycloalkyl, or heterocycloalkyl molecules used herein can be substituted or unsubstituted. As used herein, the term substituted includes the addition of an alkoxy, aryloxy, amino, alkyl, alkenyl, alkynyl, aryl, heteroalkyl, heteroalkenyl, heteroalkynyl, heteroaryl, cycloalkyl, or heterocycloalkyl group to a position attached to the main chain of the alkoxy, aryloxy, amino, alkyl, alkenyl, alkynyl, aryl, heteroalkyl, heteroalkenyl, heteroalkynyl, heteroaryl, cycloalkyl, or heterocycloalkyl, e.g., the replacement of a hydrogen by one of these molecules. Examples of substitution groups include, but are not limited to, hydroxy, halogen (e.g., F, Br, Cl, or I), and carboxyl groups. Conversely, as used herein, the term unsubstituted indicates the alkoxy, aryloxy, amino, alkyl, alkenyl, alkynyl, aryl, heteroalkyl, heteroalkenyl, heteroalkynyl, heteroaryl, cycloalkyl, or heterocycloalkyl has a full complement of hydrogens, i.e., commensurate with its saturation level, with no substitutions, e.g., linear decane (—$(CH_2)_9$—$CH_3$).

In other examples, the tyrosine kinase inhibitor is selected from the group consisting of nilotinib (TASIGNA®), bosutinib (BOSULIF®), dasatinib (SPRYCEL®), sorafenib (Nexavar®), pazopanib (Votrient®), sunitinib (SUTEN®), ponatinib (ICLUSIG®), getfitinib, erlotinib, and a compound having the formula of Formula II wherein,
$X_1$ is N or CH;
$R^1$ is —OH or —$OCH_3$;
Y is $C_{6-10}$ aryl substituted with $R^2$, or $C_{5-10}$ heteroaryl substituted with $R^2$ or N-methylpiperazinyl;
$R^2$ is —$(CH_2)_n$—$R^3$, —$(CH_2)_n$—$C(O)$—$R^3$, or —$O(CH_2)_n$—$R^3$;
$R^3$ is —H, —CN, halogen, $C_{1-3}$ alkyl, $C_{1-3}$ alkoxy, phenyl, pyridinyl, amino, di $C_{1-3}$ alkylamino, di $C_{1-3}$ alkylamino, hydroxyl $C_{1-3}$ alkylamino, carboxy $C_{1-3}$ alkylamino, $C_{3-6}$ cycloalkyl $C_{1-3}$ alkylamino, pyrrolidinyl, hydroxyl pyrrolidinyl, hydroxyl $C_{1-3}$ alkyipyrolidinyl, carboxypyrrolidinyl, piperidinyl, $C_{1-3}$ alkylpiperidinyl, di $C_{1-3}$ alkyl piperidinyl, piperazinyl, $C_{1-3}$ alkylpiperazinyl, $C_{1-4}$ alkoxycarbonylpiperazinyl, or morpholinyl; and
n is an integer selected from 0 to 3,
or an isomer or pharmaceutically acceptable salt thereof.

In the methods provided herein, $R^3$ of a compound having Formula II can be —H, —CN, halogen, $C_{1-3}$ alkyl, $C_{1-3}$ alkoxy, phenyl, pyridinyl, amino, ethylamino, diethylamino, pyrrolidinyl, piperidinyl, piperazinyl, morpholinyl or any one selected from the group consisting of the structural formula shown below As used herein, the term pharmaceutically acceptable salt refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. Pharmaceutically acceptable salts of the compounds provided herein, for example, pharmaceutically acceptable salts of nilotinib, bosutinib pazopanib and a compound of Formula I, include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesuifonate, formate, fumarate, glucoheptonate, glycerophosphate, gluconate, hemi sulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, tdfluoroacetic acid, undecanoate, valerate salts, and the like.

In the methods provided herein, the compound having the formula of Formula II can be a compound having the formula of Formula III as shown below.

III

The compound represented by Formula III is also known as LCB 03-0110 or 3-(2-(3-(morpholinomethyl)phenyl)thieno [3,2-b]pyridine-7-ylamino)phenol. Compounds having the formula of Formula II or Formula III are inhibitors of the discoidin domain receptor (DDR) tyrosine kinases, which include DDR1 and DDR2.

The compounds described herein can be prepared in a variety of ways. The compounds can be synthesized using various synthetic methods. At least some of these methods are known in the art of synthetic organic chemistry. The compounds described herein can be prepared from readily available starting materials. Optimum reaction conditions can vary with the particular reactants or solvent used, but such conditions can be determined by one skilled in the art by routine optimization procedures.

Variations on Formula I of Formula II include the addition, subtraction, or movement of the various constituents as described for each compound. Similarly, when one or more chiral centers are present in a molecule, all possible chiral variants are included.

Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts, Greene's Protective Groups in Organic Synthesis, 5th. Ed., Wiley & Sons, 2014, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., or $^{13}C$) infrared spectroscopy, spectrophotometry (e.g., UV-visible), or mass spectrometry, or by chromatography such as high performance liquid chromatography (HPLC) or thin layer chromatography.

Methods of making a compound having the formula of Formula II or the formula of Formula III are also provided in U.S. Patent Application Publication No. 2013/0072482, which is hereby incorporated herein in its entirety by this reference. Methods of making nilotinib and derivatives thereof are provided in U.S. Pat. No. 7,169,791, which is hereby incorporated herein in its entirety by this reference. Methods of making bosutinib and derivatives thereof are provided in U.S. Pat. No. 6,002,008, which is hereby incorporated herein in its entirety by this reference. Methods of making pazopanib and derivatives thereof are provided in U.S. Pat. No. 7,105,530, which is hereby incorporated herein in its entirety by this reference. The methods include the use of tyrosine kinase inhibitors, including nilotinib (TASIGNA®), bosutinib (BOSULIF®), dasatinib (SPRYCEL®), sorafenib (Nexavar®), pazopanib (Votrient®), sunitinib (SUTENT®), ponatinib (ICLUSIG®), LCB 03-0110, compounds having Formula I, compounds having Formula II, compounds having Formula or derivatives thereof that cross the blood brain barrier. Any of the compounds described herein can be modified to enhance blood-brain barrier permeability. Optionally, one or more of the compounds described herein can be administered with an agent that enhances the blood brain barrier permeability of the compound(s).

Also provided are methods of promoting lysosomal clearance in one or more cells of a subject comprising administering to the subject that has a disorder associated with decreased lysosomal clearance an effective amount of a tyrosine kinase inhibitor, wherein the tyrosine kinase inhibitor is not Gleevec. As used throughout, lysosomal clearance is a process by which accumulating lipids, proteins, glycoproteins or a combination thereof are metabolized or degraded in the lysosome of one or more cells in the subject. A decrease in lysosomal clearance means a decrease in degradation of lipids, proteins and/or glycoproteins in the lysosome of one or more cells of the subject as compared to a control, for example as compared to lysosomal clearance in one or more cells of a healthy subject. Any disorder associated with decreased lysosomal clearance can be treated using the methods provided herein, including, but limited to, any of the LSDs set forth throughout. As used herein, references to promoting or increasing include a change of 10%, 20%, 30%, 40%, 50%, 60%, 70%, 80%, 90% 100%, 200%, 400% or greater as compared to a control level. Optionally, promoting lysosomal clearance decreases the amount of a lipid, a protein, a glycoprotein or a combination thereof in existing aggregates in the lysosome of one or more cells in a subject. Optionally, promoting lysosomal clearance inhibits or prevents formation of aggregates comprising a lipid, a protein, a glycoprotein or a combination thereof in the lysosome of one or more cells in a subject, Optionally, promoting lysosomal clearance decreases the amount of time required to degrade or metabolize a lipid, a protein, a glycoprotein or a combination thereof in one or more cells of the subject as compared to a control.

Optionally, in the methods provided herein, the effective amount of the tyrosine kinase inhibitor inhibits or prevents toxic substance aggregation in one or more cells of the subject as compared to a control. As used herein, references to decreasing, reducing, or inhibiting include a change of 10%, 20%, 30%, 40%, 50%, 60%, 70%, 8090% or greater as compared to a control level. Such terms can include, but do not necessarily include, complete elimination of the toxic substance in one or more cells of the subject. Optionally, the one or more cells are brain cells, cells in one or more peripheral tissues of the subject, or a combination thereof. Optionally, the brain cells can be neurons and/or glial cells. In the methods provided herein, a toxic substance that can aggregate or accumulate in cells can be one or more of a lipid, a protein or a glycoprotein. The toxic substance(s) can increase cell damage and/or increase cell death in one or more cells of the subject. In the methods provided herein, the toxic substance(s) can be in the lysosome or elsewhere in one or more cells of the subject. For example, and not to be limiting, LSDs characterized by an accumulation of lipids in the cells of a subject include, but are not limited to, sphingolipidoses (including Gaucher's and Niemann-Pick diseases), gangliosidosis (including Tay-Sachs disease), leukodystrophies; mucopolysaccharidoses (including Hunter syndrome and Hurler disease), glycoprotein storage disorders, mucolipidoses, and glycogen storage disease type II (Pompe disease).

Lipids and glycoprotiens that accumulate in sphingolipidoses include sphingomyelin in brain and red blood cells (Nieman Pick Disease); glycoplipids, including ceramide trihexosi de, in brain heart and kindey (Fabry disease); galactocerebroside in oligondendrocytes (Krabbe disease); glucocerebrosides in red blood cells, spleen and liver (Gaucher disease); GM2 gangliosides in neurons (Tay-Sachs disease) and Sandhoff disease; GM1 gangliosides; and sulfatide compounds in neural tissue (metachromatic leukodystrophy).

Lysosomal storage diseases also include mucopolysaccharidoses (MP) that have a deficiency in one or more lysosomal enzymes, for example, α-L-iduronidate (Hurler disease, Scheie syndrome and Hurler Schei syndome); iduronate sulphate (hunter disease) heparan sulfate (Sanfilipo type A), N-acetyl-α-D-glucosatifine (Sanfilipo type B), CoA-α-glucosaminide-N-aceteltytranfer (Sanfilipo type C), N-Acetyl-α-D-glucosaminide-6-sulfate (Sanfilipo type D and Morquio syndrome type A), B-galactose (Morquio syndrome type B) and N-acetylegalatosatnine (Maroteaus-Lamy disease) but all of these MPs diseases are a result of lysosomal accumulation of heparan sulfate, dermatan sulfate or keratan sulfate. Glycogen storage diseases (i.e Pompe disease) result from storage of sugars and phosphorylated sugars in the lysosomes.

The methods provided herein optionally include selecting a subject with a LSD. One of skill in the art knows how to diagnose a subject with a LSD. For example, one or more of the following tests can be used: a genetic test (e.g., identification of a mutation associated with a LSD) or familial analysis (e.g., family history, genetic testing of parents), central nervous system imaging (e.g., magnetic resonance imaging and positron emission tomography), clinical or behavioral tests (e.g., assessments to identify mood disorders, aggressiveness and/or cognitive abnormalities), or laboratory tests (e.g, blood and/or urine tests to identify abnormal levels of metabolites or enzymatic deficiencies).

The methods provided herein optionally further include administering an effective amount of a second therapeutic agent or therapy to the subject. The second therapeutic agent or therapy can be administered to the subject prior to, simultaneously with, or subsequent to administration of the tyrosine kinase inhibitor. The second therapeutic agent or therapy is selected from the group consisting of an enzyme, hematopoietic stem cells, a bone marrow transplant, gene therapy or a small molecule. For example, and not to be limiting, LSDs associated with an enzymatic deficiency can be treated with an enzyme to increase the amount of the deficient enzyme in the subject. For example, enzyme replacement therapy (ERT) with a recombinant enzyme, such as imiglucerase (Cerezyme®), velaglucerase alfa (VPRIV®) or taliglucerase alfa (Elelyso®), can be used as a second therapeutic agent to treat Type I Gaucher disease. Small molecules that inhibit glycosylceramide synthase, for example, miglustat and eliglustat, can also be used to treat Type I Gaucher disease. A small molecule that acts as a chaperone to stabilize a defective enzyme produced by the subject or a small molecule that reduces the amount of one or more substrates that would normally be processed by an enzyme in the subject can also be used.

One or more therapeutic agents that reduce the symptoms of a LSD can also be administered. For example, an anti-epileptic such as gabapentin or lamotrigine can be used to prevent seizures in a subject. Antibiotics can be used to treat bacterial infections such as pneumonia. Other agents include, but are not limited to, anti-inflammatory agents (e.g., NSAIDs and anti-inflammatory steroids), and muscle relaxants, Dialysis, physical therapy and surgery are also contemplated herein as therapies to treat a LSD.

In some methods, the second therapeutic agent can be a second tyrosine kinase inhibitor. Therefore, in some examples, a first tyrosine kinase and a second tyrosine kinase inhibitor are administered to the subject. In the methods where a second tyrosine kinase is administered, the second tyrosine kinase can be a tyrosine kinase inhibitor that differs in selectivity for one or more receptor tyrosine kinases as compared to the first tyrosine kinase inhibitor. For example, and not to be limiting, in methods in which a first tyrosine kinase inhibitor that inhibits an Abl receptor tyrosine kinase inhibitor is administered, the second tyrosine kinase can be a tyrosine kinase inhibitor that does not inhibit an Abl receptor tyrosine kinase, a tyrosine kinase inhibitor that has increased selectivity for a. Abl receptor or a tyrosine kinase inhibitor that has decreased selectivity for a Abl receptor tyrosine as compared to the first tyrosine kinase inhibitor. In another example, in the methods in which a compound of Formula I is administered, the second tyrosine kinase inhibitor can be a tyrosine kinase inhibitor that does not inhibit DDR1 and/or DDR2 or has decreased selectivity for DDR1 and/or DDR2, as compared to a compound of Formula I.

The term effective amount, as used throughout, is defined as any amount necessary to produce a desired physiologic response. In some methods, the effective amount can be less than the amount used in chemotherapeutic methods to treat cancer or leukemia, but is an amount sufficient to promote lysosomal clearance in one or more cells of a subject, or treat a LSD in the subject. For example, the dosage is optionally less than about 10 mg/kg and can be less than about 9.5, 9, 8.5, 8, 7.5, 7, 6.5, 6, 5.5, 5, 4.5, 4, 3.5, 3, 2.5, 2, 1.5, 1.25, 1.0, 0.9, 0.8, 0.7, 0.6, 0.5, 0.4, 0.3, 0.2, 0.1 mg/kg or any dosage in between these amounts. The dosage can range from about 0.1 mg/kg to about 10 mg/kg, from about 0.1 mg/kg to about 9 mg/kg, from about 0.1 mg/kg to about 8 mg/kg, from about 0.1 mg/kg to about 7 mg/kg, from about 0.1 mg/kg to about 6 mg/kg, from about 0.1 mg/kg to about 5 mg/kg, from about 0.1 mg/kg to about 4 mg/kg, from about 0.1 mg/kg to about 3 mg/kg, from about 0.1 mg/kg to about 2 mg/kg, from about 0.1 mg/kg to about 1 mg/kg, or from about 0.1 mg/kg to about 0.5 mg/kg. One of skill in the art would adjust the dosage as described below based on specific characteristics of the inhibitor and the subject receiving it.

Furthermore, the duration of treatment can be longer in the present methods than the duration of chemotherapeutic treatment, for example cancer treatment. For example, administration to a subject with a LSD could be at least daily (e.g., once, twice, three times per day) for weeks, months, or years so long as the effect is sustained and side effects are manageable.

Effective amounts and schedules for administering one or more of the tyrosine kinase inhibitors described herein can be determined empirically and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, unwanted cell death, and the like. Generally, the dosage will vary with the type of inhibitor, the species, age, body weight, general health, sex and diet of the subject, the mode and time of administration, rate of excretion, drug combination, and severity of the particular condition and can be determined by one of skill in the art. The dosage can be adjusted by the individual physician in the event of any contraindications. Dosages can vary and can be administered in one or more dose administrations daily.

The tyrosine kinase inhibitors and other agents described herein can be provided in a pharmaceutical composition. These include, for example, a pharmaceutical composition comprising a therapeutically effective amount of one or more tyrosine kinase inhibitors and a pharmaceutical carrier. The term carrier means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject. Such pharmaceutically acceptable carriers include sterile biocompatible pharmaceutical carriers, including, but not limited to, saline, buffered saline, artificial cerebral spinal fluid, dextrose, and water.

Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the agent described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected agent without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 22nd edition, Loyd V. Allen et al, editors, Pharmaceutical Press (2012).

Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins, hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the agent(s) described herein suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof are admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyllleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

The compositions are administered in a number of ways depending on whether local or systemic treatment is desired, and on the area to be treated. The compositions are administered via any of several routes of administration, including orally, parenterally, intravenously, intraperitoneally, intracranially, intraspinally, intrathecally, intraventricularly, intramuscularly, subcutaneously, intracavity or transdermally. Pharmaceutical compositions can also be delivered locally to the area in need of treatment, for example by topical application or local injection. Effective doses for any of the administration methods described herein can be extrapolated from dose-response curves derived from in vitro or animal model test systems.

Throughout, treat, treating, and treatment refer to a method of reducing or delaying one or more effects or symptoms of LSD. The subject can be diagnosed with a disease or disorder. Treatment can also refer to a method of reducing the underlying pathology rather than just the symptoms. The effect of the administration to the subject can have the effect of, but is not limited to, reducing one or more symptoms of the LSD, a reduction in the severity of the LSD, the complete ablation of the LSD, or a delay in the onset or worsening of one or more symptoms. For example, a disclosed method is considered to be a treatment if there is about a 10% reduction in one or more symptoms of the disease in a subject when compared to the subject prior to treatment or when compared to a control subject or control value. Thus, the reduction can be about a 10, 20, 30, 40, 50, 60, 70, 80, 90, 100%, or any amount of reduction in between.

As used throughout, by subject is meant an individual. The subject can be an adult subject or a pediatric subject. Pediatric subjects include subjects ranging in age from birth to eighteen years of age. Thus, pediatric subjects of less than about 10 years of age, five years of age, two years of age, one year of age, six months of age, three months of age, one month of age, one week of age or one day of age are also included as subjects. Preferably, the subject is a mammal such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical formulations are contemplated herein.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Sanfilippo A Syndrome

A model of mucopolysaccharidosis 3A (MPSIIIA) can be used to determine the effects of any of the compounds set forth herein. Homozygous mice for the $Sgsh^{mps3a}$ mutation have only 3-4% of the wild type level of sulfamidase activity. This results in extensive lysosomal accumulation of heparin sulfate most prominently in neuronal tissue and liver and, to a lesser degree, in the spleen. GM2 ganglioside accumulation is also found. The outward phenotype of scruffy coat, hunched posture, and reduced activity is usually seen by 6 to 7 months of age. Corneal opacity is also found at approximately 7 months of age. Death occurs between 7 and 10 months of age, on average, and autopsy reveals brain lesions, hepatosplenomegaly and a distended bladder containing turbid urine. The homozygotes have thicker skullcaps, vertebral deformation, thickening of the urinary bladder wall, and bladder blockage that leads to severe bladder distention as they age. $Sgsh^{mps3a}/Sgsh^{mps3a}$ mice provide a model for the human disease mucopolysaccharidosis 3A (MPSIIIA), also known as Sanfilippo syndrome type A. The electrophoresis banding pattern of glycosaminoglycans from the brain and urine of homozygous mice is similar to the abnormal pattern found in samples from human MPSIIIA patients. The human disease symptoms include severe central nervous system degeneration, claw hand, and visceromegaly, with death occurring in the second or third decade of life (Bhaumik et al., "A mouse model for mucopolysaccharidosis type III A (Sanfillipo syndrome)," *Glycobiology* 9:1389-96 (1999); Bhattacharyya et al., "A novel missense mutation in lysosomal sulfamidase is the basis of MPSIII A in a spontaneous mouse mutant," *Glycobiology*, 11(1): 99-103 (2001). Any time, between from about four to about 10 months old, mice are treated with 0.1-10 mg/kg Niloitnib, 0.1-5 mg/kg Bosutinib, 0.1-10 mg/kg pazopanib or 0.1-5 mg/kg LCB-03-0110 to activate the autophagy-lysosome pathway in the brain and the rest of the body. To determine the effects of these drugs in Sanfilippo mouse models, homozygous and heterozygous control mice (male and female) are intraperitoneally (IP) injected daily with either the drug(s) or DMSO (placebo) for 3 weeks. Cognition and motor behavior can be determined in these mice. The mechanistic effects of these drugs on clearance of heparan sulfate via autophagy can also be determined.

Use of Tyrosine Kinase Inhibitors in a Model of Sanfilippo A Syndrome

Animals

Twelve 8-9 month old, male Sgsh transgenic mice (MPS) were used for all experiments and were compared to fourteen non-transgenic age-matched, littermates (non-TG). The symptomatic MPS mice, based on behavioral tests, were then divided into three groups (n=4) for daily intraperitoneal (I.P.) treatment with either nilotinib (10 mg/kg), bosutinib (5 mg/kg), or DMSO, and compared to the same non-TG mice which were also divided into three treatment groups (n=4, 5). Treatment lasted for 21 days. At the end of the treatment period the mice underwent behavioral testing again and Western blot analysis was performed.

Behavior

Rotarod: Mice were placed on the rotarod apparatus which sped up to 50 rpm, over the course of 5 minutes for 3-5 trials, with a minimum of 30 minutes rest between trials. Data collected were the time the animal remained ambulatory on the rotating rod, in seconds, labelled "latency to fall." Data is also presented as "percentage difference" where all groups are normalized to the non-transgenic, untreated group, assuming non-transgenic, untreated animals are preforming at 100%.

Open-field Anxiety: Mice were placed in the open field arena for 5 minutes. Animals were tracked by photocell beams along the arena floor. Data were collected and analyzed for the number of entries into the center zone of the arena, the total distance (cm) traveled within the center zone, the amount of time (sec) spent in the center zone, the total distance traveled (cm) in the peripheral wall zone of the arena, the amount of time spent (sec) in the wall zone, the total distance traveled (cm) during the 5 minute trial, the total time spent moving 'total ambulatory time' (sec) during the 5 minute trial, and the average velocity (cm/sec) during the 5 minute trial.

Open-field Locomotion: Mice were placed in the open field arena for 60 minutes. Animals were tracked by photocell beams along the arena floor. Data were collected and analyzed for total locomotion via total cm travelled. Other data collected were the total time spent moving 'total ambulatory time' (sec) during the 60 minute trial and the average velocity (cm/sec) during the 60 minute trial.

Protein Extraction and Western Blot

Brain, heart and liver were isolated from the nilotinib and bosutinib treated mice and compared with DMSO treated mice. Tissues were homogenized in 1× Sodium Tris EDTA NP40 (STEN) lysis buffer [50 mM sodium Tris (pH 7.6), 150 mM NaCl, 2 mM EDTA, 0.2% NP-40, 0.2% BSA, 20 mM PMSF and protease cocktail inhibitor], centrifuged at 10000 g for 20 min at 48° C., and the supernatant containing the soluble protein fraction was collected. The supernatant was analyzed by western blot on SDS-NuPAGE Bis-Tris gel (Invitrogen (Carlsbad, Calif.)). Heparin Sulfate was probed with (1:1000) anti-heparin sulfate antibody (Millipore (Billerica, Mass.)), Lamp2 was probed with (1:1000) anti-Lamp2 antibody (Invitrogen), and actin was probed with (1:1000) anti-actin antibody (Millipore).

Results

Figure 1:
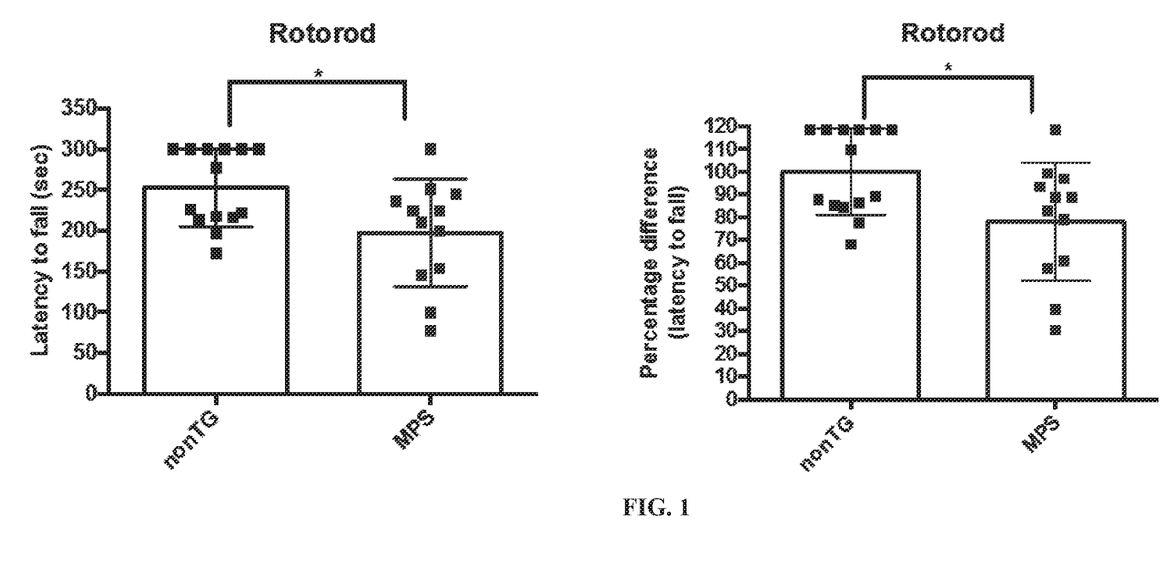
FIG. 1 shows rotarod results before treatment (pre-treatment) with tyrosine kinase inhibitors of male Sgsh transgenic mice (MPS) versus non-transgenic (non-TG) littermate mice. The left panel and the right panel show that the MPS mice have significantly lower latency to fall compared to littermate non-TG controls. T-test: unpaired, type 2, 2 tailed, *p>0.05. p=0.02.

Rotarod: FIG. 1 (left panel and right panel) shows that the MPS mice have a significantly lower latency to fall compared to littermate non-TG controls. Therefore, these mice have decreased performance on the rotarod test. These results show that NIPS mice have motor and/or balance problems.

Figure 2A:
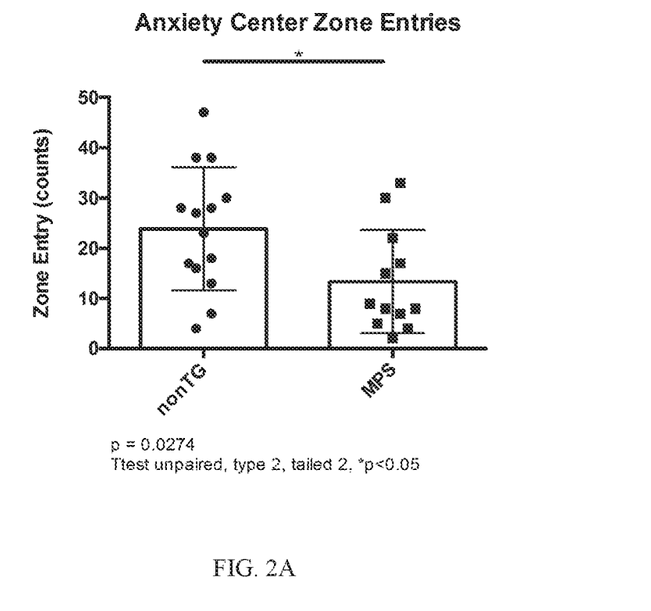
FIG. 2A shows that MPS mice had significantly lower center zone entries than non-Tg control littermates, and therefore spent less time in the center zone. This suggests that MPS have increased anxiety and fear-like behavior compared to littermate non-TG controls. p=0.0274, t-test unpaired, type 2, tailed 2, *p<0.05.
Figure 2B:
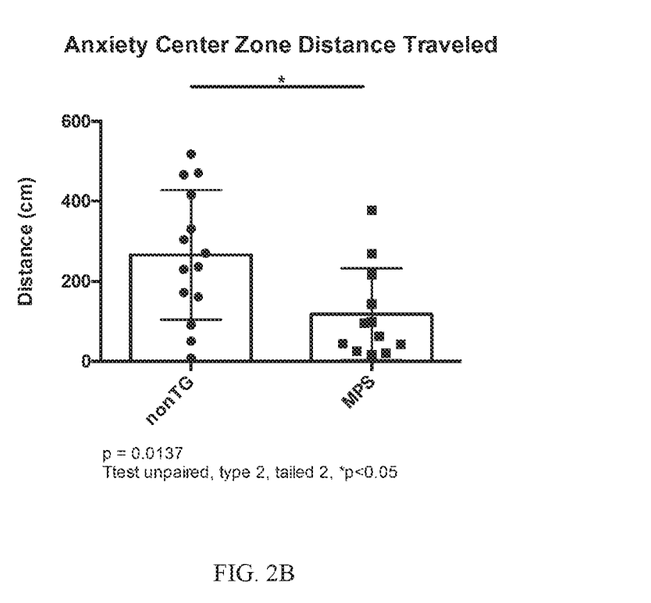
FIG. 2B shows that MPS mice travel less within the center zone. This suggests that MPS have increased anxiety and fear-like behavior compared to littermate non-TG controls. p=0.0137, t-test unpaired, type 2, tailed 2, *p<0.05.
Figure 2C:
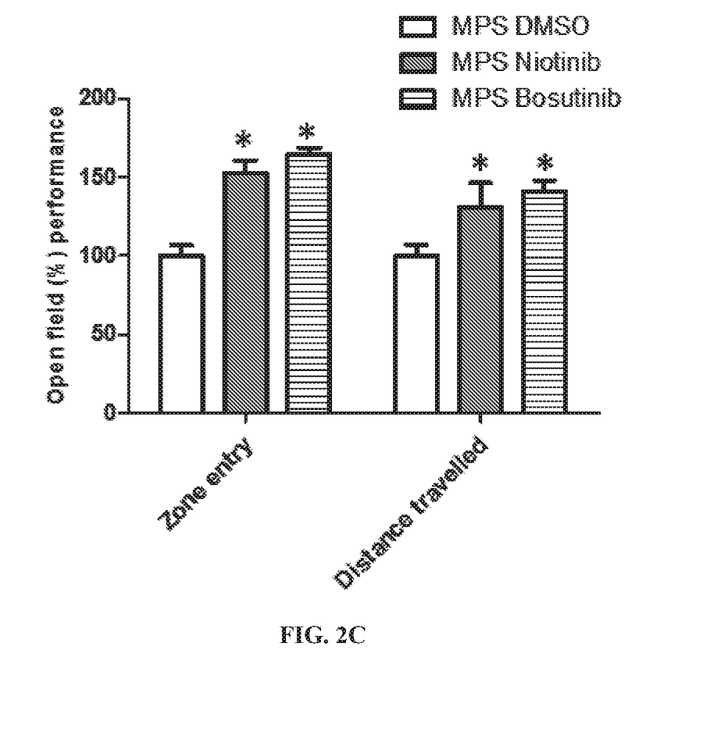
FIG. 2C shows that treatment with nilotinib or bosutinib reduces anxiety (more entries into center zone, p<0.05) and increases overall locomotion (p<0.05) activity of MPS mice.

Behavior: FIG. 2 shows that the MPS mice have significantly lower center zone entries than Non-Tg control littermates (FIG. 2, left panel). Therefore, MPS mice spent less time in the center zone and traveled less within the center zone. (FIG. 2B) This shows that MPS mice have increased anxiety and fear-like behavior compared to littermate non-TG controls (FIGS. 2A and 2B). However, treatment with nilotinib or bosutinib reduced anxiety (more entries into center zone, $p<0.05$) and increased the overall locomotion ($p<0.05$) activity of MPS mice (FIG. 2C).

Figure 3:
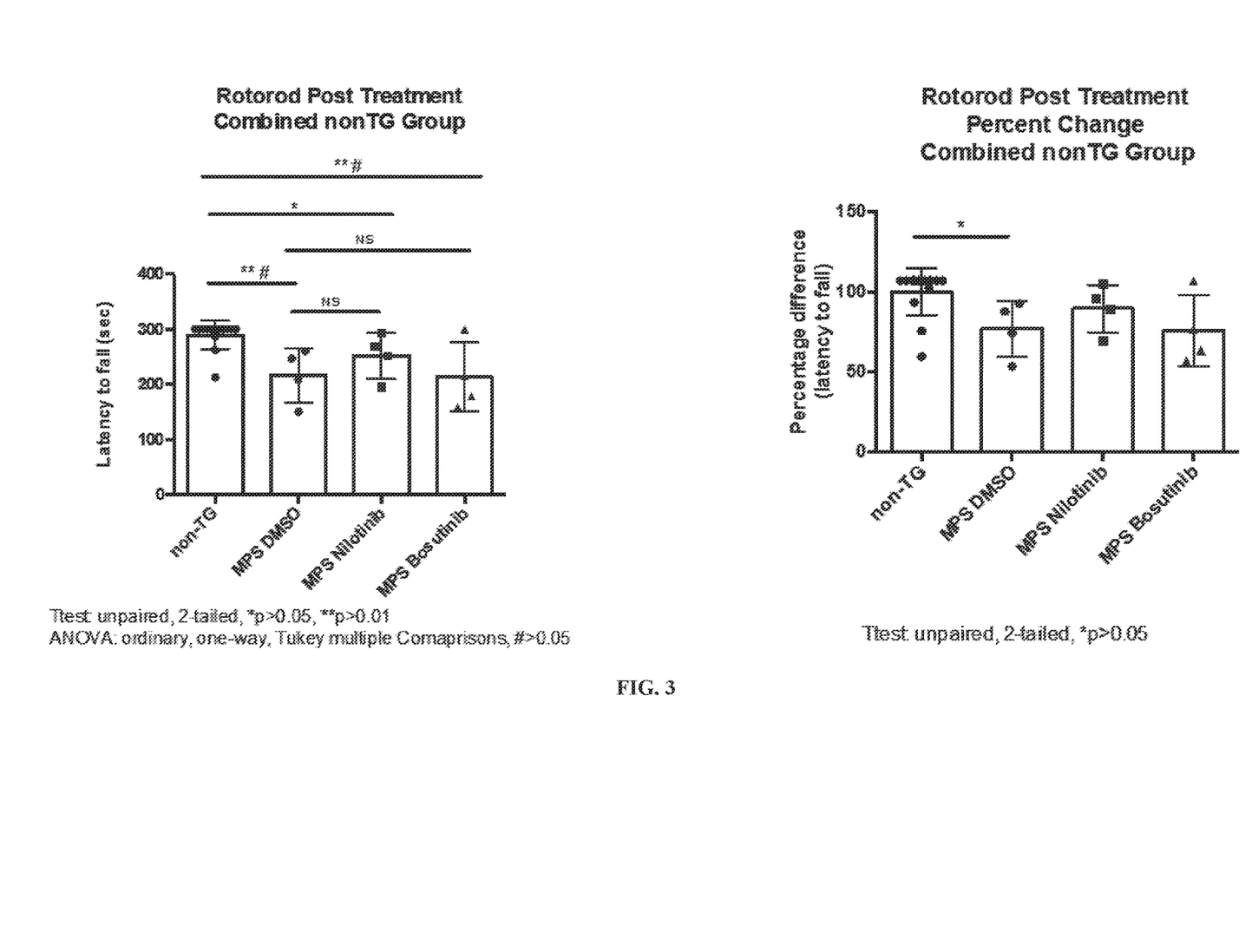
FIG. 3 shows that MPS mice treated with DMSO showed significantly lower performance on the rotarod tests compared to the age-matched non-TG littermate control group (left panel and right panel), via t-test and Analysis of Variance (ANOVA). However, the MPS mice treated with nilotinib performed better, as compared to MPS mice treated with DMSO or bosutinib, and look more like the non-TG controls.

Post-treatment rotarod MPS versus non-TG littermate mice: After the behavioral tests were conducted the symptomatic MPS mice were divided into three groups (n=4). The groups were treated daily for 21 days I.P. with either nilotinib (10 mg/kg), bosutinib (5 mg/kg), or DMSO. There were three control groups made of age matched non-TG littermate controls (n=4, 5) which were treated in the same way. Behavioral tests were repeated and data collected is referred to as "post-treatment." Since there was no significant difference between the control non-TG treatment groups, they were combined into one non-TG control group. The MPS mice treated with DMSO showed significantly lower performance on the rotarod, compared to the age-matched non-TG littermate control group via t-test and Analysis of Variance (ANOVA) (FIG. 3, left panel and right panel). However, the MPS mice treated with nilotinib perform better than the MPS mice treated with DMSO or bosutinib, and look more like the non-TG controls. This suggests that nilotinib could help ameliorate some of the symptoms of a lysosomal storage disease.

Western blot: After behavioral testing was completed, the mice were euthanized and tissue samples were collected for protein analysis. Brain, heart, and liver were collected from each of the mice and the soluble proteins were isolated from each tissue sample. Western blot analysis was performed for heparan sulfate, lysosome associated membrane protein (LAMP 2), and actin as a protein loading control.

Figure 4A:
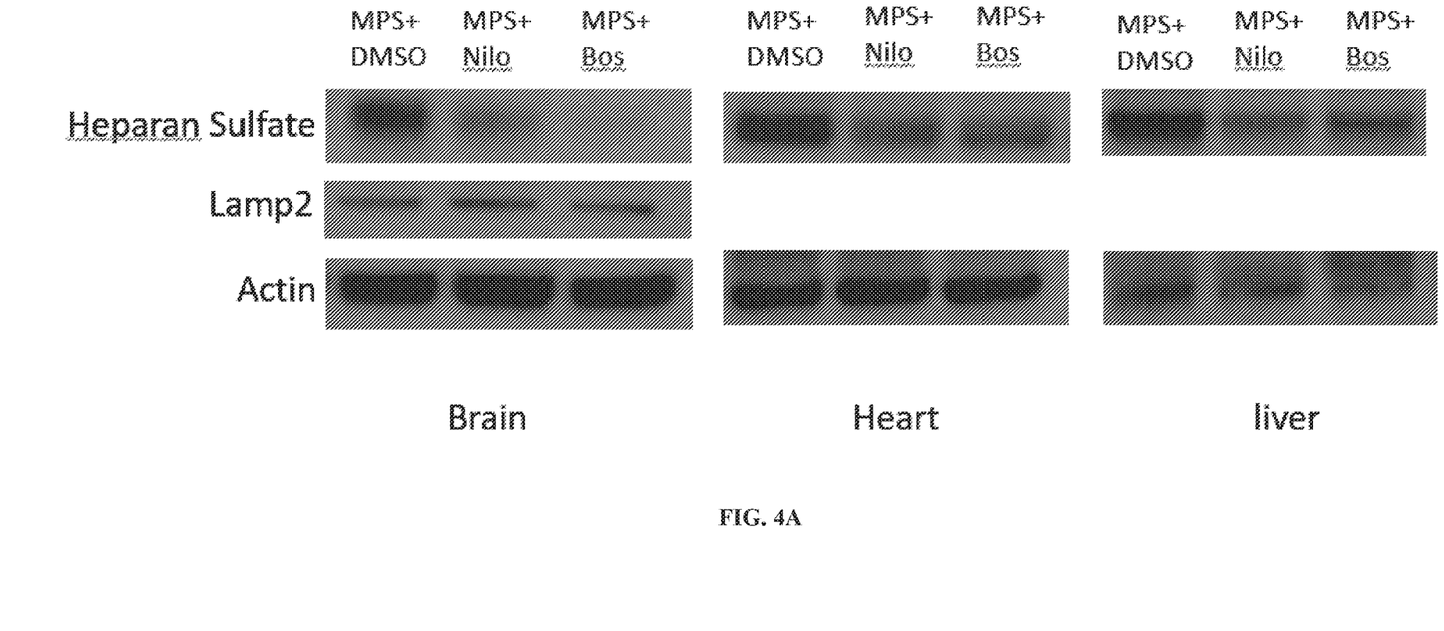
FIG. 4A is a Western blot showing that MPS mice treated with DMSO have an increase in heparan sulfate in the brain, heart and liver compared to MPS treated with either nilotinib for bosutinib. This shows that the MPS mice are unable to effectively clear these polysaccharides, but treatment with the tyrosine kinase inhibitors nilotinib and bosutinib rescue the ability to clear heparan sulfate both centrally in the brain and peripherally in the heart and the liver. LAMP2 was also measured as a marker for the lysosome. There was a significant difference in the amount of LAMP2 measured in the brain.
Figure 4B:
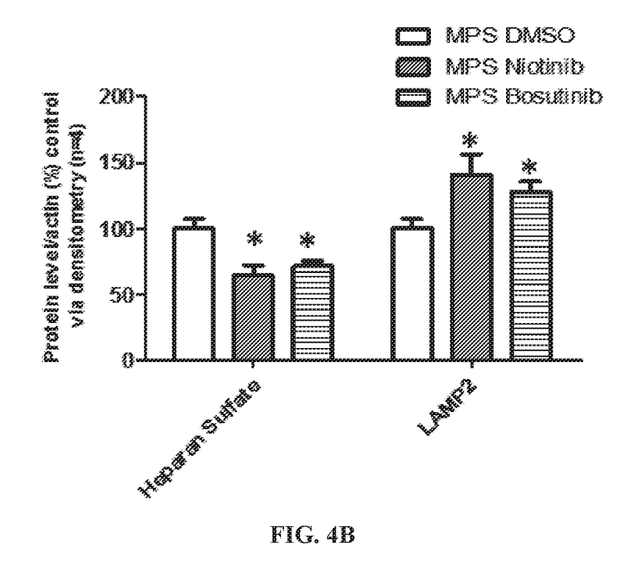
FIG. 4B provides densitometry results of Western blots showing that heparan sulfate is significantly reduced (*p<0.05, n=4, T-test) while LAMP2 is significantly increased (*p<0.05, n=4, T-test) in the brain.

The Western blot shows that MPS mice treated with DMSO have an increase in heparan sulfate compared to MPS treated with either nilotinib for bosutinib in the brain, heart and liver (FIG. 4a). This shows that the MPS mice are unable to effectively clear these polysaccharides, but treatment with tyrosine kinase inhibitors, for example, nilotinib and bosutinib, can rescue the ability to clear heparan sulfate both centrally in the brain and peripherally in the heart and the liver. Reduction of heparin sulfate results in the liver, heart and brain result in behavioral improvement. LAMP2 was also measured as a marker for the lysosome. In the brain there is a significant difference in the amount of LAMP2 measured, suggesting that there is de novo biogenesis of lysosomes with nilotinib or bosutinib treatment compared to DMSO (FIG. 4a). It is likely that these drugs increase the efficiency of lysosomal clearance of heparan sulfate via increased biogenesis of lysosomes. The densitometry results of Western blots show that heparan sulfate is significantly reduced (*p<0.05, n=4, T-test), while LAMP2 is significantly increased (*p<0.05, n=4, T-test) in the brain (FIG. 4b).

Sanfilippo B Syndrome

Mucopolysaccharidosis type III (MPS III) (Sanfilippo B syndrome) is a pediatric autosomal recessive neurological disorder that leads to early death. Affected children suffer from progressive neurological deterioration, including cognitive and motor defects, which result from severe neurodegeneration reminiscent of adult neurodegenerative diseases. The primary biochemical defect is deficiency of the lysosomal enzyme alpha-N-acetylglucosaminidase (Naglu), leading to accumulation of heparan sulfate throughout the body and brain. There are no effective treatments for Sanfilippo B disease and animal models of the disease exhibit hearing and vision impairments that may interfere with behavioral testing. To evaluate the effects of tyrosine kinase inhibitors on lysosomal clearance of heparan sulfate, mutant male Sanfilippo B mice (B6.129S6-Naglu$^{tm1Efn/J}$ backbred onto C57BL6/J; (Lonskaya et al. *Neuroscience* 304: 316-327 (2015); Naglu$^{-/-}$) can be crossed with heterozygous females (Naglu$^{+/-}$) to obtain homozygous mice and heterozygous controls as previously described (Kan et al. *Behav Brain Res.* 312: 265-271 (2016). These mice develop hearing and vision impairment as they age. At six months, mice can be treated with niloitnib or bosutinib to activate the autophagy-lysosome pathway in the brain and the rest of the body. To determine the effects of these drugs in this model, at any time from about 4 to about 10 months old, mice are treated intraperitoneally with 0.1-10 mg/kg Niloitnib, 0.1-5 mg/kg Bosutinib, 0.1-11.0 mg/kg pazopanib or 0.1-5 mg/kg LCB-03-0110 to activate the autophagy-lysosome pathway in the brain and the rest of the body. Mice are injected intraperitoneally (IP) injected daily with either the drug(s) or DMSO (Placebo) for 3 weeks. Cognition and motor behavior can be determined in these mice. The mechanistic effects of these drugs on clearance of heparan sulfate via autophagy can also be determined.

Behavioral tests are conducted prior to sacrifice of animals. Cell death in specific neuronal subtypes is assessed and a corresponding behavioral evaluation is performed to determine whether tyrosine kinase inhibitors (TKIs) affect a) cognition via Morris water maze (memory) and open field test (anxiety); and b) neurotransmitters including acetylcholinesterase (AchE) activity via ELISA. Whether TKIs affect motor behavior via rotarod and light beam tests is also assessed. Metabolism of dopamine, TH+ neurons and homovanillic acid (HVA) via ELISA and IHC is also analyzed, Whether TKIs lead to survival of neurons via IHC, Nissl staining, and caspase-3 activity is determined.

What is claimed is:

1. A method for treating Sanfillipo syndrome A or Sanfillipo syndrome B in a subject comprising administering to the subject having Sanfillipo syndrome A or Sanfillipo syndrome B an effective amount of nilotinib or bosutinib, wherein the effective amount is about 10 mg/kg/day or less.

2. The method of claim 1, wherein the subject is a pediatric subject.

3. The method of claim 1, wherein the effective amount of the nilotinib or bosutinib inhibits or prevents toxic substance aggregation in one or more cells of the subject.

4. The method of claim 3, wherein the one or more cells are brain cells, cells in one or more peripheral tissues of the subject, or a combination thereof.

5. The method of claim 4, wherein the brain cells are neurons and/or glial cells.

6. The method of claim 1, further comprising administering a second therapeutic agent or therapy to the subject.

7. The method of claim 6, wherein the second therapeutic agent or therapy is selected from the group consisting of: enzyme replacement therapy, gene therapy, a hematopoietic stem cell transplant and a small molecule.

* * * * *